(12) United States Patent
Sirianni et al.

(10) Patent No.: US 11,807,661 B2
(45) Date of Patent: Nov. 7, 2023

(54) ANTIBODY FUSION PROTEIN AND RELATED COMPOSITIONS FOR TARGETING CANCER

(71) Applicants: Dignity Health, Phoenix, AZ (US); Arizona Board of Regents on Behalf of Arizona State University, Scottsdale, AZ (US)

(72) Inventors: Rachael Sirianni, San Francisco, CA (US); Rebecca Cook, Scottsdale, AZ (US); Tsafrir Mor, Tempe, AZ (US); Joseph Blattman, Scottsdale, AZ (US)

(73) Assignees: Dignity Health, San Francisco, CA (US); Arizona Board of Regents on Behalf of Arizona State University, Tempe, AZ (US)

( * ) Notice: Subject to any disclaimer, the term of this patent is extended or adjusted under 35 U.S.C. 154(b) by 501 days.

(21) Appl. No.: 16/929,001

(22) Filed: Jul. 14, 2020

(65) Prior Publication Data

US 2020/0339679 A1 Oct. 29, 2020

Related U.S. Application Data

(62) Division of application No. 15/999,241, filed as application No. PCT/US2017/018472 on Feb. 17, 2017, now Pat. No. 10,745,478.

(60) Provisional application No. 62/297,502, filed on Feb. 19, 2016.

(51) Int. Cl.
| | |
|---|---|
| A61K 35/00 | (2006.01) |
| C07K 16/28 | (2006.01) |
| A61K 47/68 | (2017.01) |
| C12N 15/82 | (2006.01) |
| A61P 35/00 | (2006.01) |
| A61K 9/00 | (2006.01) |
| C12N 15/86 | (2006.01) |
| C12N 15/74 | (2006.01) |
| A61K 39/00 | (2006.01) |

(52) U.S. Cl.
CPC ............ *C07K 16/28* (2013.01); *A61K 9/0019* (2013.01); *A61K 47/6817* (2017.08); *A61P 35/00* (2018.01); *C07K 16/2809* (2013.01); *C12N 15/743* (2013.01); *C12N 15/8258* (2013.01); *C12N 15/86* (2013.01); *A61K 2039/505* (2013.01); *C07K 2317/56* (2013.01); *C07K 2317/622* (2013.01); *C07K 2319/33* (2013.01); *C07K 2319/55* (2013.01)

(58) Field of Classification Search
None
See application file for complete search history.

(56) References Cited

U.S. PATENT DOCUMENTS

2015/0329637 A1 11/2015 Urech et al.

FOREIGN PATENT DOCUMENTS

WO WO2016/014974 * 1/2016

OTHER PUBLICATIONS

Yankelevich et al. (Pediatric Blood Cancer 2012, 59(7): 1198-1205) (Year: 2012).*
Dardevet et al. (Toxin Mar. 2015, 7(4):1079-1101). (Year: 2015).*
Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
UniProt Q9UADO Neurotoxin BmK CT (Sep. 16, 2015), http://rest.uniprot.org/uniprotkb/Q9UADO.txt, retrieved Jan. 11, 2023, 3 pages.
Patent Cooperation Treaty, International Search Report and Written Opinion, International Application No. PCT/2017/018472, dated Jul. 31, 2017, 6 pages.
Canada Intellectual Property Office, Examiner's Report, Application No. 3,053,242, dated Feb. 23, 2023, 4 pages.

* cited by examiner

*Primary Examiner* — Meera Natarajan
(74) *Attorney, Agent, or Firm* — Polsinelli PC

(57) ABSTRACT

Disclosed herein are compositions comprising a polypeptide with at least two domains, wherein the first domain is capable of binding CD3 and the second domain is capable of binding to a cancer cell. Also disclosed herein are methods of treating cancer in a subject, comprising: providing a composition comprising a polypeptide with at least two domains, wherein the first domain is capable of binding CD3 and the second domain is capable of binding to a cancer cell; and treating the cancer by administering a therapeutically effective dosage of the composition to the subject.

16 Claims, 5 Drawing Sheets

Specification includes a Sequence Listing.

Figure 7: Calcium flux
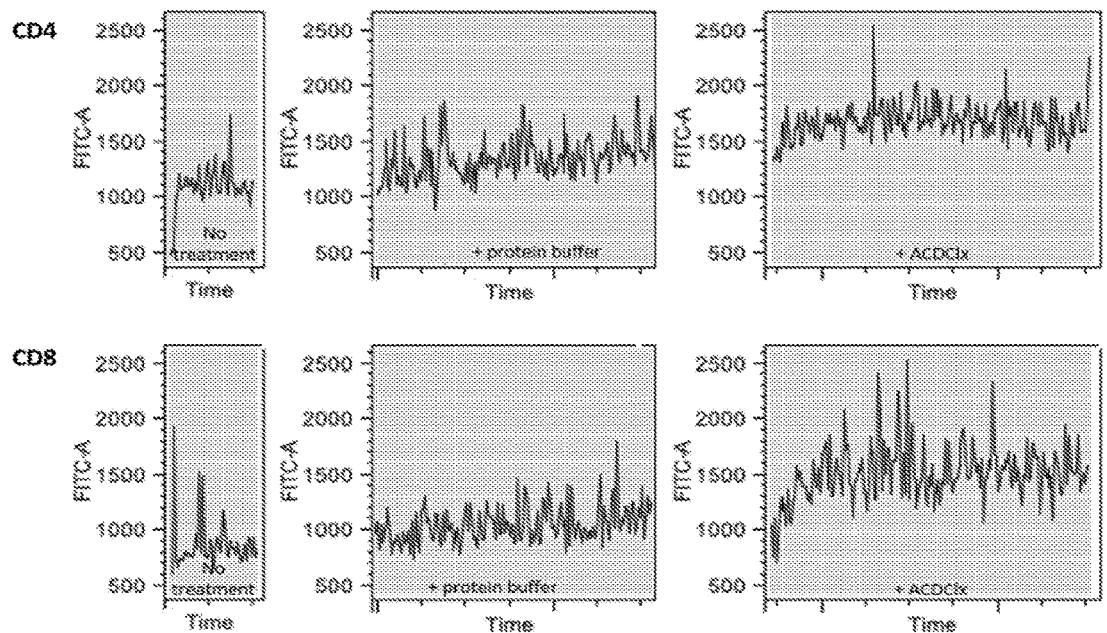
Figure 8: CD69
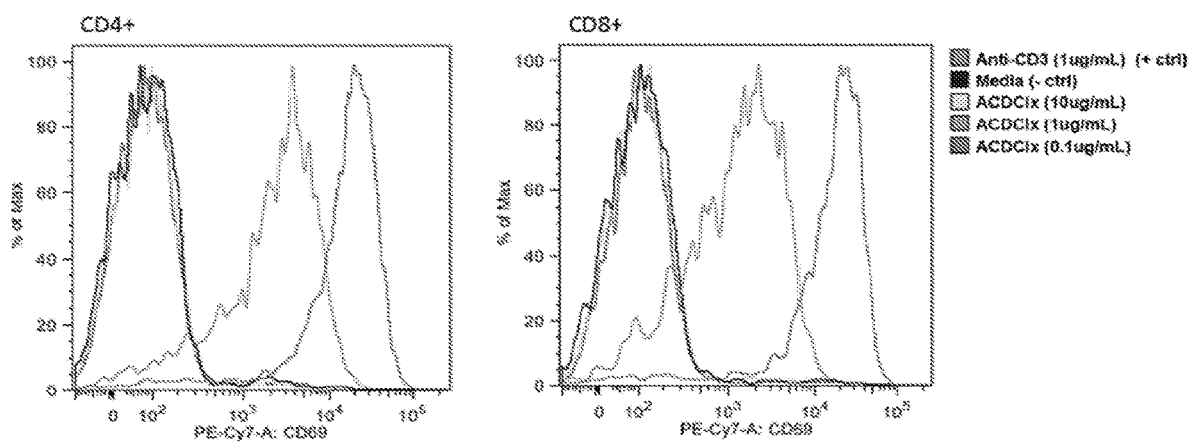

SEQUENCE LISTING

<160> NUMBER OF SEQ ID NOS: 13

<210> SEQ ID NO 1
<211> LENGTH: 116
<212> TYPE: PRT
<213> ORGANISM: Mus musculus

<400> SEQUENCE: 1

Glu Val Gln Leu Val Glu Ser Gly Gly Gly Leu Val Gln Pro Gly Lys
1               5                   10                  15

Ser Leu Lys Leu Ser Cys Glu Ala Ser Gly Phe Thr Phe Ser Gly Tyr
            20                  25                  30

Gly Met His Trp Val Arg Gln Ala Pro Gly Arg Gly Leu Glu Ser Val
        35                  40                  45

Ala Tyr Ile Thr Ser Ser Ile Asn Ile Lys Tyr Ala Asp Ala Val
    50                  55                  60

Lys Gly Arg Phe Thr Val Ser Arg Asp Asn Ala Lys Asn Leu Leu Phe
65                  70                  75                  80

Leu Gln Met Asn Ile Leu Lys Ser Glu Asp Thr Ala Met Tyr Tyr Cys
                85                  90                  95

Ala Arg Phe Asp Trp Asp Lys Asn Tyr Trp Gly Gln Gly Thr Met Val
            100                 105                 110

Thr Val Ser Ser
        115

<210> SEQ ID NO 2
<211> LENGTH: 138
<212> TYPE: PRT
<213> ORGANISM: Homo sapiens

<400> SEQUENCE: 2

Met Asp Trp Val Trp Thr Leu Leu Phe Leu Leu Ser Val Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser
    130                 135

<210> SEQ ID NO 3
<211> LENGTH: 106
<212> TYPE: PRT
<213> ORGANISM: Mus musculus

<400> SEQUENCE: 3

Gln Met Thr Gln Ser Pro Ser Ser Leu Pro Ala Ser Leu Gly Asp Arg
1               5                   10                  15

```
Val Thr Ile Asn Cys Gln Ala Ser Gln Asp Ile Ser Asn Tyr Leu Asn
             20                  25                  30

Trp Tyr Gln Gln Lys Pro Gly Lys Ala Pro Lys Leu Leu Ile Tyr Tyr
             35                  40                  45

Thr Asn Lys Leu Ala Asp Gly Val Pro Ser Arg Phe Ser Gly Ser Gly
 50                  55                  60

Ser Gly Arg Asp Ser Ser Phe Thr Ile Ser Ser Leu Glu Ser Glu Asp
65                  70                  75                  80

Ile Gly Ser Tyr Tyr Cys Gln Gln Tyr Tyr Asn Tyr Pro Trp Thr Phe
                 85                  90                  95

Gly Pro Gly Thr Lys Leu Glu Ile Lys Arg
            100                 105

<210> SEQ ID NO 4
<211> LENGTH: 128
<212> TYPE: PRT
<213> ORGANISM: Homo sapiens

<400> SEQUENCE: 4

Met Asp Phe Gln Val Gln Ile Phe Ser Phe Leu Leu Ile Ser Ala Ser
1               5                  10                  15

Val Ile Ile Ser Arg Gly Gln Ile Val Leu Thr Gln Ser Pro Ala Ile
             20                  25                  30

Met Ser Ala Ser Pro Gly Glu Lys Val Thr Met Thr Cys Ser Ala Ser
             35                  40                  45

Ser Ser Val Ser Tyr Met Asn Trp Tyr Gln Gln Lys Ser Gly Thr Ser
 50                  55                  60

Pro Lys Arg Trp Ile Tyr Asp Thr Ser Lys Leu Ala Ser Gly Val Pro
65                  70                  75                  80

Ala His Phe Arg Gly Ser Gly Ser Gly Thr Ser Tyr Ser Leu Thr Ile
                 85                  90                  95

Ser Gly Met Glu Ala Glu Asp Ala Ala Thr Tyr Tyr Cys Gln Gln Trp
            100                 105                 110

Ser Ser Asn Pro Phe Thr Phe Gly Ser Gly Thr Lys Leu Glu Ile Asn
            115                 120                 125

<210> SEQ ID NO 5
<211> LENGTH: 15
<212> TYPE: PRT
<213> ORGANISM: Artificial Sequence
<220> FEATURE:
<223> OTHER INFORMATION: Made in laboratory

<400> SEQUENCE: 5

Gly Gly Gly Gly Ser Gly Gly Gly Gly Ser Gly Gly Gly Gly Ser
1               5                  10                  15

<210> SEQ ID NO 6
<211> LENGTH: 36
<212> TYPE: PRT
<213> ORGANISM: Leiurus quinquestriatus

<400> SEQUENCE: 6

Met Cys Met Pro Cys Phe Thr Thr Asp His Gln Met Ala Arg Lys Cys
1               5                  10                  15

Asp Asp Cys Cys Gly Gly Lys Gly Arg Gly Lys Cys Tyr Gly Pro Gln
             20                  25                  30

Cys Leu Cys Arg
```

-continued

<210> SEQ ID NO 7
<211> LENGTH: 36
<212> TYPE: PRT
<213> ORGANISM: Artificial Sequence
<220> FEATURE:
<223> OTHER INFORMATION: Made in laboratory

<400> SEQUENCE: 7

```
Met Cys Met Pro Cys Phe Thr Thr Asp His Gln Met Ala Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg
        35
```

<210> SEQ ID NO 8
<211> LENGTH: 5
<212> TYPE: PRT
<213> ORGANISM: Artificial Sequence
<220> FEATURE:
<223> OTHER INFORMATION: Made in laboratory

<400> SEQUENCE: 8

```
Gly Gly Gly Gly Ser
1               5
```

<210> SEQ ID NO 9
<211> LENGTH: 293
<212> TYPE: PRT
<213> ORGANISM: Artificial Sequence
<220> FEATURE:
<223> OTHER INFORMATION: Made in laboratory

<400> SEQUENCE: 9

```
Met Glu Val Gln Leu Val Glu Ser Gly Gly Gly Leu Val Gln Pro Gly
1               5                   10                  15

Lys Ser Leu Lys Leu Ser Cys Glu Ala Ser Gly Phe Thr Phe Ser Gly
            20                  25                  30

Tyr Gly Met His Trp Val Arg Gln Ala Pro Gly Arg Gly Leu Glu Ser
        35                  40                  45

Val Ala Tyr Ile Thr Ser Ser Ile Asn Ile Lys Tyr Ala Asp Ala
    50                  55                  60

Val Lys Gly Arg Phe Thr Val Ser Arg Asp Asn Ala Lys Asn Leu Leu
65                  70                  75                  80

Phe Leu Gln Met Asn Ile Leu Lys Ser Glu Asp Thr Ala Met Tyr Tyr
                85                  90                  95

Cys Ala Arg Phe Asp Trp Asp Lys Asn Tyr Trp Gly Gln Gly Thr Met
            100                 105                 110

Val Thr Val Ser Ser Gly Gly Gly Ser Gly Gly Gly Ser Gly
        115                 120                 125

Gly Gly Ser Gln Met Thr Gln Ser Pro Ser Leu Pro Ala Ser
    130                 135                 140

Leu Gly Asp Arg Val Thr Ile Asn Cys Gln Ala Ser Gln Asp Ile Ser
145                 150                 155                 160

Asn Tyr Leu Asn Trp Tyr Gln Gln Lys Pro Gly Lys Ala Pro Lys Leu
                165                 170                 175

Leu Ile Tyr Tyr Thr Asn Lys Leu Ala Asp Gly Val Pro Ser Arg Phe
            180                 185                 190
```

```
Ser Gly Ser Gly Ser Gly Arg Asp Ser Ser Phe Thr Ile Ser Ser Leu
        195                 200                 205

Glu Ser Glu Asp Ile Gly Ser Tyr Tyr Cys Gln Gln Tyr Tyr Asn Tyr
    210                 215                 220

Pro Trp Thr Phe Gly Pro Gly Thr Lys Leu Glu Ile Lys Arg Gly Gly
225                 230                 235                 240

Gly Gly Ser Met Cys Met Pro Cys Phe Thr Thr Asp His Gln Met Ala
            245                 250                 255

Arg Lys Cys Asp Asp Cys Cys Gly Gly Lys Gly Arg Gly Lys Cys Tyr
                260                 265                 270

Gly Pro Gln Cys Leu Cys Arg Leu Glu Val Leu Phe Gln Gly Pro His
            275                 280                 285

His His His His His
        290

<210> SEQ ID NO 10
<211> LENGTH: 293
<212> TYPE: PRT
<213> ORGANISM: Artificial Sequence
<220> FEATURE:
<223> OTHER INFORMATION: Made in laboratory

<400> SEQUENCE: 10

Met Glu Val Gln Leu Val Glu Ser Gly Gly Gly Leu Val Gln Pro Gly
1               5                   10                  15

Lys Ser Leu Lys Leu Ser Cys Glu Ala Ser Gly Phe Thr Phe Ser Gly
            20                  25                  30

Tyr Gly Met His Trp Val Arg Gln Ala Pro Gly Arg Gly Leu Glu Ser
        35                  40                  45

Val Ala Tyr Ile Thr Ser Ser Ile Asn Ile Lys Tyr Ala Asp Ala
    50                  55                  60

Val Lys Gly Arg Phe Thr Val Ser Arg Asp Asn Ala Lys Asn Leu Leu
65                  70                  75                  80

Phe Leu Gln Met Asn Ile Leu Lys Ser Glu Asp Thr Ala Met Tyr Tyr
                85                  90                  95

Cys Ala Arg Phe Asp Trp Asp Lys Asn Tyr Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Gln Met Thr Gln Ser Pro Ser Ser Leu Pro Ala Ser
    130                 135                 140

Leu Gly Asp Arg Val Thr Ile Asn Cys Gln Ala Ser Gln Asp Ile Ser
145                 150                 155                 160

Asn Tyr Leu Asn Trp Tyr Gln Gln Lys Pro Gly Lys Ala Pro Lys Leu
                165                 170                 175

Leu Ile Tyr Tyr Thr Asn Lys Leu Ala Asp Gly Val Pro Ser Arg Phe
            180                 185                 190

Ser Gly Ser Gly Ser Gly Arg Asp Ser Ser Phe Thr Ile Ser Ser Leu
        195                 200                 205

Glu Ser Glu Asp Ile Gly Ser Tyr Tyr Cys Gln Gln Tyr Tyr Asn Tyr
    210                 215                 220

Pro Trp Thr Phe Gly Pro Gly Thr Lys Leu Glu Ile Lys Arg Gly Gly
225                 230                 235                 240

Gly Gly Ser Met Cys Met Pro Cys Phe Thr Thr Asp His Gln Met Ala
            245                 250                 255
```

Arg Lys Cys Asp Asp Cys Cys Gly Gly Lys Gly Arg Gly Arg Cys Tyr
            260                 265                 270

Gly Pro Gln Cys Leu Cys Arg Leu Glu Val Leu Phe Gln Gly Pro His
            275                 280                 285

His His His His His
            290

<210> SEQ ID NO 11
<211> LENGTH: 336
<212> TYPE: PRT
<213> ORGANISM: Artificial Sequence
<220> FEATURE:
<223> OTHER INFORMATION: Made in laboratory

<400> SEQUENCE: 11

Met Asp Trp Val Trp Thr Leu Leu Phe Leu Leu Ser Val Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Gly Gly Gly Gly Ser Gly
    130                 135                 140

Gly Gly Gly Ser Gly Gly Gly Gly Ser Met Asp Phe Gln Val Gln Ile
145                 150                 155                 160

Phe Ser Phe Leu Leu Ile Ser Ala Ser Val Ile Ile Ser Arg Gly Gln
                165                 170                 175

Ile Val Leu Thr Gln Ser Pro Ala Ile Met Ser Ala Ser Pro Gly Glu
            180                 185                 190

Lys Val Thr Met Thr Cys Ser Ala Ser Ser Ser Val Ser Tyr Met Asn
        195                 200                 205

Trp Tyr Gln Gln Lys Ser Gly Thr Ser Pro Lys Arg Trp Ile Tyr Asp
    210                 215                 220

Thr Ser Lys Leu Ala Ser Gly Val Pro Ala His Phe Arg Gly Ser Gly
225                 230                 235                 240

Ser Gly Thr Ser Tyr Ser Leu Thr Ile Ser Gly Met Glu Ala Glu Asp
                245                 250                 255

Ala Ala Thr Tyr Tyr Cys Gln Gln Trp Ser Ser Asn Pro Phe Thr Phe
            260                 265                 270

Gly Ser Gly Thr Lys Leu Glu Ile Asn Gly Gly Gly Ser Met Cys
        275                 280                 285

Met Pro Cys Phe Thr Thr Asp His Gln Met Ala Arg Lys Cys Asp Asp
    290                 295                 300

Cys Cys Gly Gly Lys Gly Arg Gly Lys Cys Tyr Gly Pro Gln Cys Leu
305                 310                 315                 320

```
Cys Arg Leu Glu Val Leu Phe Gln Gly Pro His His His His His
            325                 330                 335
```

<210> SEQ ID NO 12
<211> LENGTH: 336
<212> TYPE: PRT
<213> ORGANISM: Artificial Sequence
<220> FEATURE:
<223> OTHER INFORMATION: Made in laboratory

<400> SEQUENCE: 12

```
Met Asp Trp Val Trp Thr Leu Leu Phe Leu Leu Ser Val Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Gly Gly Gly Gly Ser Gly
    130                 135                 140

Gly Gly Gly Ser Gly Gly Gly Gly Ser Met Asp Phe Gln Val Gln Ile
145                 150                 155                 160

Phe Ser Phe Leu Leu Ile Ser Ala Ser Val Ile Ile Ser Arg Gly Gln
                165                 170                 175

Ile Val Leu Thr Gln Ser Pro Ala Ile Met Ser Ala Ser Pro Gly Glu
            180                 185                 190

Lys Val Thr Met Thr Cys Ser Ala Ser Ser Ser Val Ser Tyr Met Asn
        195                 200                 205

Trp Tyr Gln Gln Lys Ser Gly Thr Ser Pro Lys Arg Trp Ile Tyr Asp
    210                 215                 220

Thr Ser Lys Leu Ala Ser Gly Val Pro Ala His Phe Arg Gly Ser Gly
225                 230                 235                 240

Ser Gly Thr Ser Tyr Ser Leu Thr Ile Ser Gly Met Glu Ala Glu Asp
                245                 250                 255

Ala Ala Thr Tyr Tyr Cys Gln Gln Trp Ser Ser Asn Pro Phe Thr Phe
            260                 265                 270

Gly Ser Gly Thr Lys Leu Glu Ile Asn Gly Gly Gly Ser Met Cys
        275                 280                 285

Met Pro Cys Phe Thr Thr Asp His Gln Met Ala Arg Lys Cys Asp Asp
    290                 295                 300

Cys Cys Gly Gly Lys Gly Arg Gly Arg Cys Tyr Gly Pro Gln Cys Leu
305                 310                 315                 320

Cys Arg Leu Glu Val Leu Phe Gln Gly Pro His His His His His
            325                 330                 335
```

<210> SEQ ID NO 13

<211> LENGTH: 882
<212> TYPE: DNA
<213> ORGANISM: Artificial Sequence
<220> FEATURE:
<223> OTHER INFORMATION: Made in laboratory

<400> SEQUENCE: 13

```
atggaggttc agcttgttga gtctggtgga ggtttggtgc aacctggaaa gtccctcaag      60
ctctcctgtg aggcctctgg attcaccttc agcggttacg gcatgcactg ggtcaggcaa     120
gctccaggta ggggtctcga gagcgtggcc tacattacta gctccagtat taacatcaaa     180
tacgctgacg ctgtgaaggg taggttcacc gtgtccagag acaacgccaa gaacttgctc     240
ttccttcaga tgaacattct caagtctgag gacacagcca tgtactactg tgctagattc     300
gactgggaca aaaattactg gggccaagga acaatggtca ccgtttcctc aggaggagga     360
ggatcaggag gaggaggatc aggaggagga ggatcacaga tgacccagtc tccatcatca     420
ctccctgcct ccctcggaga cagagttact atcaactgtc aggccagcca ggacattagc     480
aattacttga actggtacca gcaaaagcca ggtaaggctc ctaagctcct catctactat     540
acaaacaagt tggccgatgg agtgccatca aggttcagcg gttctggttc tggaagagat     600
tcttctttca ctatctccag cctcgaatcc gaagatattg gatcttacta ctgtcaacag     660
tactacaact atccgtggac attcggacct ggtaccaagc tcgaaatcaa gaggggagga     720
ggaggatcaa tgtgtatgcc ttgctttaca acggatcatc agatggcaag gaagtgtgac     780
gactgttgtg gaggcaaggg aaggggaaag tgttacggcc cacaatgtct ctgtcgtctt     840
gaggttctct tccaaggacc tcaccatcac catcaccatt aa                         882
```

ANTIBODY FUSION PROTEIN AND RELATED COMPOSITIONS FOR TARGETING CANCER

The present application claims the benefit of priority under 35 U.S.C. § 120 as a divisional of U.S. patent application Ser. No. 15/999,241, filed on Aug. 17, 2018, which claims the benefit of priority as a 371 of international application PCT/US2017/18472, filed on Feb. 17, 2017, which claims the benefit under 35 U.S.C. § I 19(e) of provisional application serial number 62/297,502, filed Feb. 19, 2016. Each of these applications is incorporated by reference herein in its entirety.

FIELD OF THE INVENTION

The present disclosure relates to compositions and methods for the treatment of cancer.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cancer or malignant tumor is one of the leading causes of death. Cancer has a major impact on society in the United States and across the world. According to the National Cancer Institute, in 2016, an estimated 1.68 million new cases of cancer is diagnosed in the United States. Thus, there remains a need in the art for novel and effective treatments of cancers.

SUMMARY OF THE DISCLOSURE

Various embodiments disclosed herein include a composition comprising a polypeptide with at least two domains, wherein the first domain is capable of binding CD3 and the second domain is capable of binding to a cancer cell. In one embodiment, the polypeptide is a single chain polypeptide. In one embodiment, the cancer is a neuroectodermal cancer. In one embodiment, the first domain comprises variable heavy (VH) and the variable light (VL) polypeptide chains of an anti-CD3 antibody. In one embodiment, the VH polypeptide comprises the sequence set forth in SEQ ID NO: 1 or SEQ ID NO: 2, or a polypeptide sequence having at least 80% sequence identity to SEQ ID NO: 1 or SEQ ID NO: 2. In one embodiment, the VL polypeptide comprises the sequence set forth in SEQ ID NO: 3 or SEQ ID NO: 4, or a polypeptide sequence having at least 80% sequence identity to SEQ ID NO: 3 or SEQ ID NO: 4. In one embodiment, the first domain further comprises a first polypeptide linker between VH and VL polypeptides. In one embodiment, the first polypeptide linker comprises the sequence set forth in SEQ ID NO: 5, or a polypeptide sequence having at least 80% sequence identity to SEQ ID NO: 5. In one embodiment, the first domain is derived from an antibody targeting human, non human primate, or mouse CD3 receptor complex. In one embodiment, the second domain comprises a chlorotoxin peptide. In one embodiment, the second domain comprises a chlorotoxin-like peptide, such as CITx-a,b,c,d, BmKCL1, Lqh-8:6, Be ISA, Bell, AmmP2 and GaTxl. In one embodiment, the second domain comprises a peptide having a sequence set forth in SEQ ID NO: 6 or SEQ ID NO: 7, or a polypeptide sequence having at least 80% sequence identity to SEQ ID NO: 6 or SEQ ID NO: 7. In one embodiment, the composition further comprises a second polypeptide linker between the first and second domain. In one embodiment, the second polypeptide linker has a sequence Gly-Gly-Gly-Gly-Ser, as set forth in SEQ ID NO 8. In one embodiment, the composition has a sequence as set forth in SEQ ID NO: 9, SEQ ID NO: 10, SEQ ID NO: 11, or SEQ ID NO: 12, or a polypeptide sequence having at least 80% sequence identity to SEQ ID NO: 9, SEQ ID NO: 10, SEQ ID NO: 11, or SEQ ID NO: 12.

Various embodiments disclosed herein also include a method of treating cancer in a subject, comprising: providing a composition comprising a polypeptide with at least two domains, wherein the first domain is capable of binding CD3 and the second domain is capable of binding to a cancer cell; and treating the cancer by administering a therapeutically effective dosage of the composition to the subject. In one embodiment, the cancer is of neuroectodermal origin. In one embodiment, the cancer is glioblastoma (GBM). In one embodiment, the cancer cell comprises peripheral neuroectodermal tumors (PNET). In one embodiment, the cancer is medulloblastoma, neuroblastoma, ganglioneuroma, melanoma, adrenal pheochromocytoma, primitive PNET, small cell lung carcinoma, and/or Ewing's sarcoma. In one embodiment, the subject is a mammal. In one embodiment, the subject is a human.

Various embodiments disclosed herein also include a method of expressing a protein comprising: designing a DNA-coding sequence corresponding to the protein; cloning the DNA-coding sequence into a viral-based vector; transfecting the resulting vector into a plant-specific class of bacteria; infiltrating a plant with the resulting bacteria culture; and harvesting the protein from the plant after a pre-determined time. Other embodiments disclosed herein include a method of expressing a protein comprising: designing a DNA-coding sequence corresponding to the protein; cloning the DNA-coding sequence into a viral-based vector; transfecting the resulting vector into a host cell; and extracting the protein from the host cell after a pre-determined time. In one embodiment, the host cell may be a bacterial cell, a plant cell, a yeast cell or a mammalian cell. In one embodiment, the protein comprises a polypeptide with at least two domains, wherein the first domain is capable of binding CD3 and the second domain is capable of binding to a target cell of neuroectodermal origin. In one embodiment, the protein is a recombinant single chain polypeptide comprising chlorotoxin, a linker, and a domain capable of binding CD3. In one embodiment, the protein further comprises six histidine residues (His-tag) at the C-terminus or the N-terminus of the protein. In one embodiment, the method further comprises optimizing the DNA-coding sequence to promote high expression and increased yield of the protein. In one embodiment, the viral-based vector comprises a tobacco mosaic virus-based vector, or a bean yellow dwarf virus-based vector. In one embodiment, the plant-specific class of bacteria is *Agrobacterium tumefaciensa*. In one embodiment, the plant is *N benthn.miana*. In one embodiment, the protein is harvested from a leaf tissue of the plant.

Various embodiments disclosed herein also include a method of purifying a recombinant protein expressed in a plant-based expression system comprising: blending plant tissues comprising the recombinant protein; and enriching the recombinant protein through sequential centrifugation and re-suspension in buffers. Other embodiments disclosed herein include a method of purifying a recombinant protein expressed in a plant-based expression system comprising: blending plant tissues comprising the recombinant protein; centrifuging the blended tissues and discarding the supernatant; re-suspending the pellet in detergent, and discarding the supernatant; re-suspending and incubating the pellet comprising the recombinant protein in denaturing or reducing buffer; centrifuging and discarding the pellet; diluting the supernatant comprising the recombinant protein in refolding buffer; and concentrating the purified and refolded protein to the desired concentration. In one embodiment, the denaturing buffer comprises urea (e.g., 8M Urea). In one embodiment, the denaturing buffer comprises DTT. In one embodiment, the refolding buffer comprises Tris-HCl, NaCl, and oxidized L-glutathione.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

FIG. 7 depicts, in accordance with embodiments herein, calcium flux in CD4+ or CD8+ T cells (as indicated by an increase in Fluo-4 AM fluorescence intensity using FITC excitation/emission filter) was measured immediately after mixing GL261-LucNeo mouse glioma cells with freshly isolated mouse splenocytes with (1) nothing adding, (2) ACDC1x protein buffer (no ACDC1x), or (3) ACDC1x added. Calcium flux is an indicator of initial T cell activation.

FIG. 8 depicts, in accordance with embodiments herein, CD4+ and CD8+ T cell activation as measured by CD69 expression 11 hours post-treatment. Treatments were incubated with freshly isolated mouse splenocytes (B6 background) and confluent GL261-LucNeo mouse GBM cells. GBM cells in 1 ug/mL ACDC1x group were all dead, which corresponds to killing by T cells and correlates with CD69 activation on T cells.

DESCRIPTION OF THE INVENTION

Figure 1:
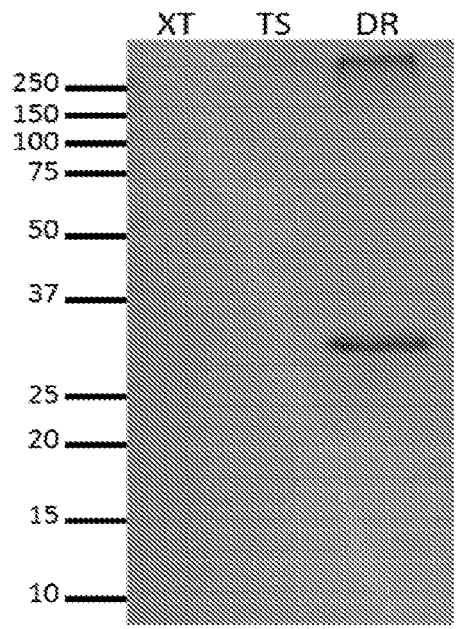
FIG. 1 depicts, in accordance with embodiments herein, ACDC1x cannot be extracted from the soluble fraction (XT) nor the Triton-soluble fraction (TS). ACDC1x can be extracted from the Triton-insoluble fraction using denaturing and reducing (DR) buffer.
Figure 2:
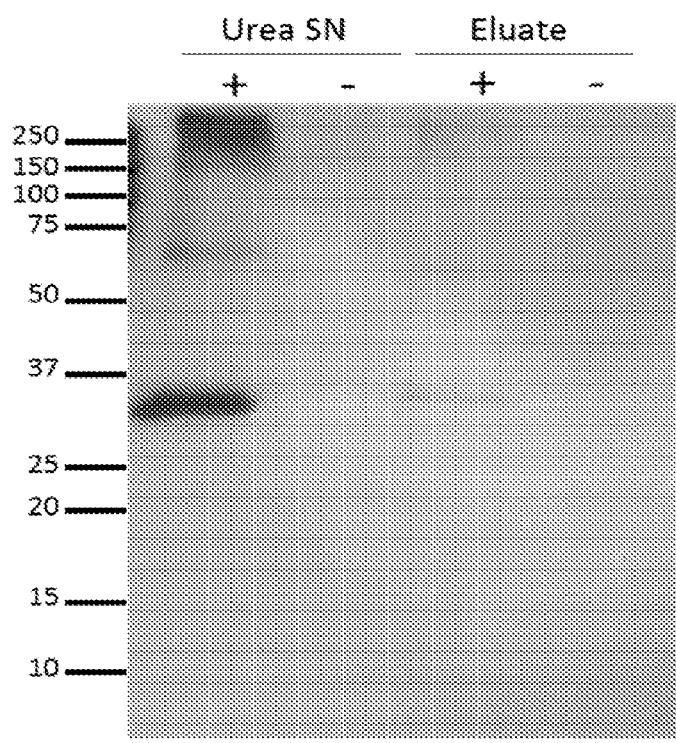
FIG. 2 depicts, in accordance with embodiments herein, ACDC1x is not detected under non-reducing conditions (−), suggesting the His-tag may be folded inside of the fusion protein if ACDC1x is not refolded under controlled conditions.
Figure 3:
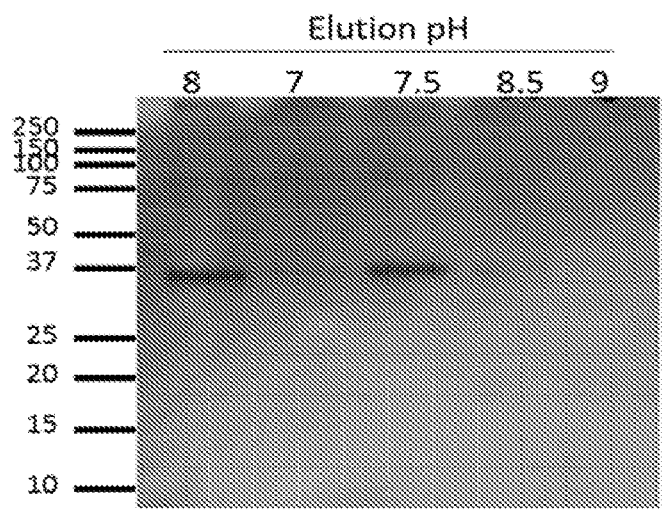
FIG. 3 depicts, in accordance with embodiments herein, optimization of Tris-HCl pH-ACDC1x is eluted in the greatest yield using pH 7.5 and 8.
Figure 4:
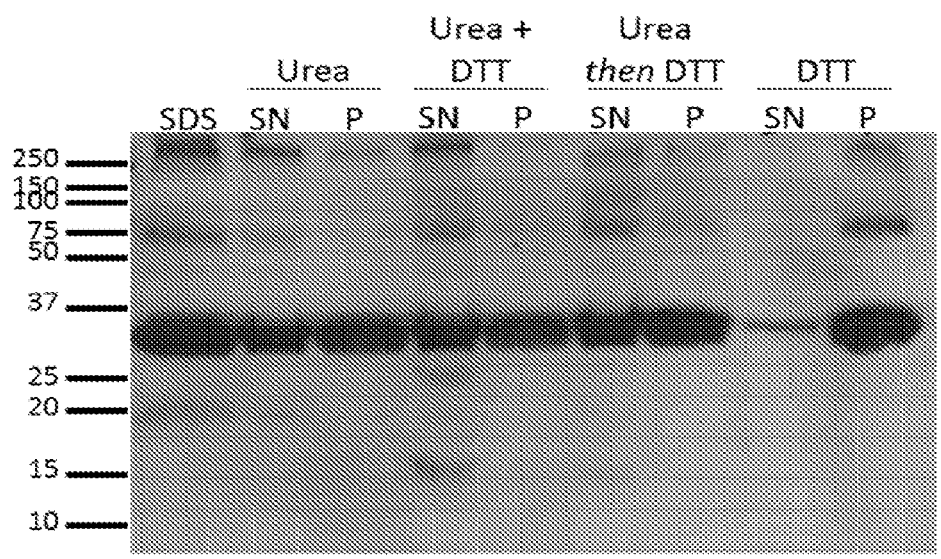
FIG. 4 depicts, in accordance with embodiments herein, addition of DTT does not reduce the solubilization efficiency of ACDC1x, and thus is a good candidate for use as a reducing agent prior to refolding.
Figure 5:
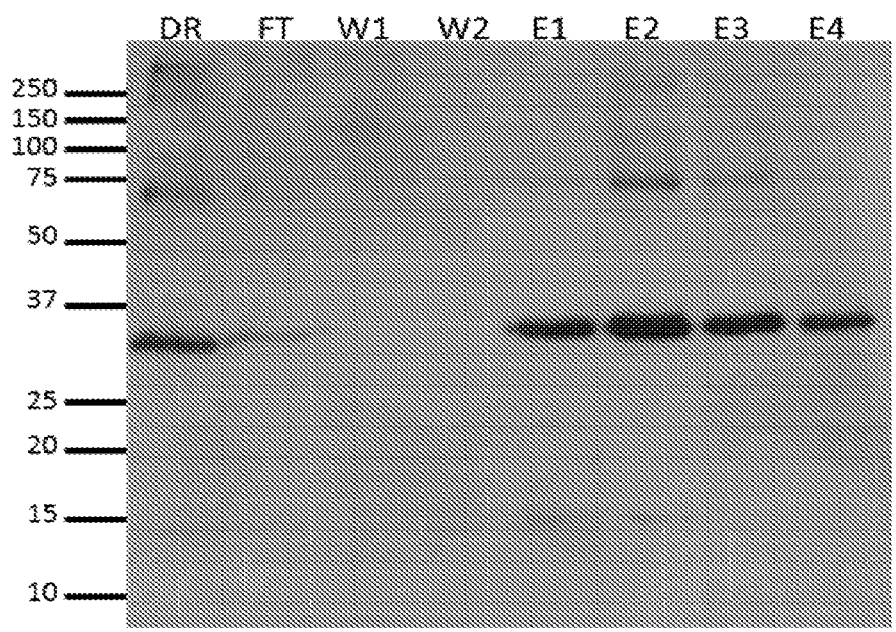
FIG. 5 depicts, in accordance with embodiments herein, ACDC1x can be detected in the eluates following purification and refolding on-column.
Figure 6:
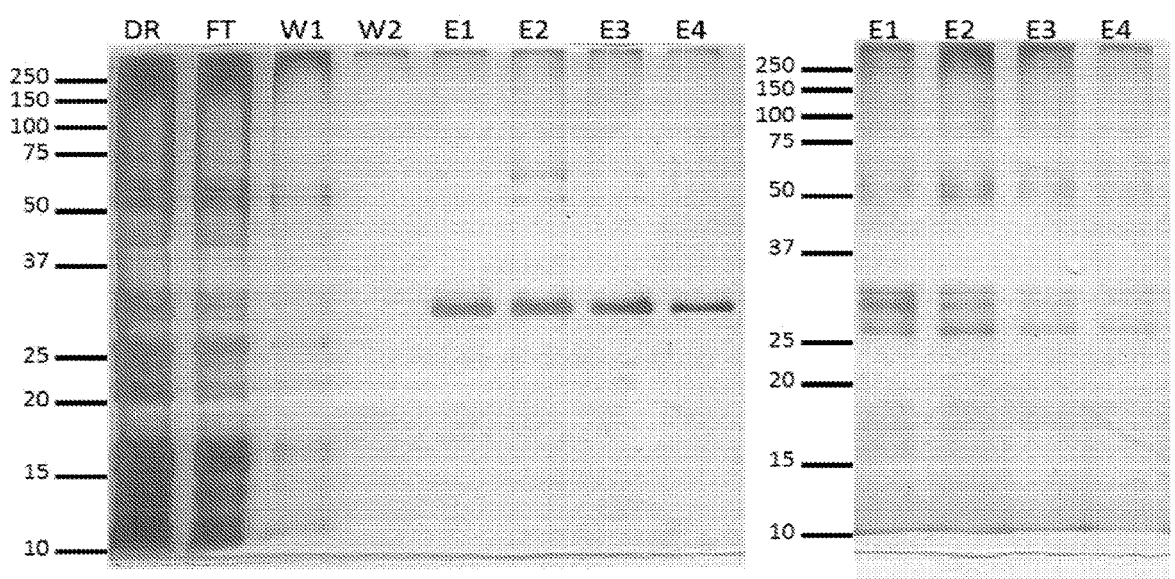
FIG. 6 depicts, in accordance with embodiments herein, an example of the purity of ACDC1x that can be obtained after a His-tag purification. Protein content was resolved under reducing (left) and non-reducing conditions (right).

All references cited herein are incorporated by reference in their entirety as though fully set forth. Unless defined otherwise, technical and scientific terms used herein have the same meaning as commonly understood by one of ordinary skill in the art to which this invention belongs.

Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the terms "peptide," "polypeptide," or "protein" refers to a molecule composed of two or more monomers (amino acids) linearly linked by amide bonds (also known as peptide bonds), or by secondary linkages such as disulfide bonds. The term "polypeptide" refers to any chain or chains of two or more amino acids, and does not refer to a specific length of the product. The terms "peptide," "polypeptide," or "protein" are also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid se4uence. It may be generated in any manner, including by chemical synthesis. A "peptide," "polypeptide," or "protein" may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded or denatured.

As used herein, the terms "patient" and "subject," used interchangeably herein, refers to an individual having symptoms of, or at risk for, cancer or other malignancy. Subjects or patients may be human or non-human and may include, for example, animal strains or species used as "model systems" for research purposes, such a mouse model. A patient may include either adults or juveniles (e.g., children). The term "patient" or "subject", further refers to any living organism, preferably a mammal (e.g., human or non-human, such as, but not limited to a companion animal, farming animal, livestock, etc.) that may benefit from the administration of compositions contemplated herein.

As used herein, the terms "Ctx," "Cltx," and "chlorotoxin," used interchangeably herein, refers to a peptide or polypeptide that may be obtained from (e.g., purified and/or otherwise derived from) scorpion venom or may be produced in the laboratory (e.g., via recombinant expression).

Examples of "chlorotoxin-like" peptides include, but is not limited to, CITx-a,b,c,d, BmKCL1, Lqh-8:6, Be ISA, Bell, AmmP2 and GaTxI, as described by Ali et al, Structure activity relationship of chlorotoxin-like peptides, Toxins, 2016 8(2):36.

As used herein, the terms "cancer" and "tumor" refers to or describes the physiological condition that is typically characterized by unregulated or abnormal cell growth. Examples of cancer include, but are not limited to, carcinoma, lymphoma, blastoma, sarcoma, and leukemia.

Particular examples of cancer include glioblastoma multiforme (GBM), peripheral neuroectodermal tumors (PNET), medulloblastoma, neuroblastoma, ganglioneuroma, melanoma, adrenal pheochromocytoma, primitive PNET, small cell lung carcinoma, and/or Ewing's sarcoma. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, the term "neuroectodermal" refers to the central or peripheral nervous system. Thus, a neuroectodermal cancer would refer to a cancer in the central or peripheral nervous system and/or in the case of a malignant cancer, a cancer that originates in or has metastasized to the central or peripheral nervous system. Similarly, a cancer cell of neuroectodermal origin would refer to a cancer cell originating in the central or peripheral nervous system. Particular examples of neuroectodermal cancer includes, but is not limited to, glioblastoma, PNET, medulloblastoma, neuroblastoma, ganglioneuroma, melanoma, adrenal pheochromocytoma, primitive PNET, small cell lung carcinoma, and/or Ewing's sarcoma. In one embodiment, the term neuroectodermal may refer to cells that are derived from the same stem cell lineage that the nervous system is derived from.

As used herein, the terms "treating," "treatment" and "treat" refer to therapeutic measures that cure, slow down, ameliorate and/or halt progression of a diagnosed pathologic condition or disorder. The terms "treating," "treatment" and "treat" also refer to prophylactic or preventative measures that prevent and/or slow the development of a targeted pathologic condition or disorder. Thus, those in need of treatment include those already with the disorder; those prone to having the disorder; and those in whom the disorder is to be prevented. In some instances, a subject is successfully "treated" for cancer according to the method disclosed herein if the subject shows one or more of the following: a reduction in the number of cancer cells; absence of cancer cells; reduction in tumor size; inhibition of, or an absence of, cancer cell infiltration into peripheral organs including, for example, the spread of cancer into soft tissue and bone; inhibition of, or an absence of, tumor metastasis; inhibition of, or an absence of, tumor growth; reduced morbidity and mortality; or any combination thereof.

As further disclosed herein, the inventors have developed a novel recombinant fusion protein. The recombinant fusion protein (ACDC1x) described here is designed to engage specific cells of the immune system, such as T cells and NK T cells, against cancer cells. In one embodiment, the cancer cells are glioma cells, and the recombinant fusion protein is used for the purpose of treating brain tumors. Both CD4+T (helper) cells and CD8+(killer) T, as well as NK T cells can be engaged against glioma using this fusion protein, ACDC1x, although CD8+ T cells are expected to have the fastest and predominant anti-tumor effect. ACDC1x is a fusion of antibody-derived variable fragments targeting CD3 on the surface of mature T cells, and chlorotoxin. The anti-CD3 portion is capable of engaging T cells, while the chlorotoxin portion binds specifically to cancer cells (e.g., cancer cells of a neuroectodermal origin), with binding capability increasing with tumor grade. In one embodiment, ACDC1x brings T cells and cancer cells into immediate contact with one another to initiate T cell-killing mechanisms against the cancer cell to which the ACDC1x is bound. ACDC1x is not expected to activate T cells in the absence of a bound glioma partner and is therefore expected to be a potent, specific therapeutic to improve brain tumor treatment.

As recited above, some embodiments may provide a treatment for cancer. Moreover, some embodiments may provide that the cancer may be of a neuroectodermal origin, and may include cancers such as glioblastoma multiforme (GBM). GBM is a highly malignant form of brain tumor that affects over 11,000 patients a year in the United States alone. Due to the highly invasive nature of GBM, treating tumor cells that reside in healthy areas of the brain is extremely difficult.

With respect to conventional treatments of GBM, the blood-brain barrier (BBB) blocks over 98% of systemically administered therapeutics from entering the brain, while surgical interventions can also harm healthy tissue. As a result, the efficacy of standard of care treatments is low (e.g., administration of temozolomide), and the chance of surviving past 5 years is less than 5%. A class of therapies known as bispecific single-chain variable fragment (bs-scFv) antibodies have been shown to harness the natural abilities of the patient's own immune system to target and kill resident tumor cells.

As disclosed herein, the inventors have developed a novel fusion protein that would activate mature T cells against tumor cells. In one embodiment, the targeted immunotherapy can treat the tumor and decrease rate of tumor reoccurrence. In another embodiment, to provide treatment, the inventors linked chlorotoxin (Ctx or Cltx), a peptide able to bind cancer cells with specificity, to the T-cell activating antibody fragment of the anti-CD3 antibody, or a fragment thereof. In one embodiment, the present disclosure provides a composition comprising an ACDC1x compound. In another embodiment, the present disclosure provides a method of treating cancer, comprising providing a composition comprising an ACDC1x compound, and treating the cancer by administering a therapeutically effective dosage of the composition to a subject. In another embodiment, the cancer is of a neuroectodermal origin, such as GBM.

As further disclosed herein, in one embodiment, the present disclosure utilizes chlorotoxin, a naturally-derived peptide with demonstrated ability to target cancer cells while having little to no specificity to normal tissue. In one embodiment, systemically administered Ctx may be able to cross the blood brain barrier to reach infiltrating cells. In one embodiment described herein, Ctx can be coupled to one or more variable fragment(s) of a T cell-activating anti-CD3 antibody, forming an antibody fusion protein. By activating T cells via CD3, the requirement for T cell recognition via binding of MHC and antigen on the tumor cell is no longer necessary. This overcomes an important barrier to natural immune system-based cell killing, as cancer cells, such as for example GBM, are known to down-regulate expression of MHC on the surface as a form of immune evasion.

The fusion protein disclosed herein, ACDC1x, may be produced in plants using refined, efficient techniques to quickly produce proteins of similar structure for relatively low cost and with high yield. Importantly, this process also avoids contamination with mammalian pathogens and molecules that might be found in mammalian and bacterial systems.

By combining the ability of the anti-CD3 portion of the fusion protein to provide for T cell activation against tumor cells targeted by Ctx with the ability of Ctx to cross the BBB, the inventors improve the immune-mediated clearance of cancer cells (e.g., GBM) from surrounding healthy brain tissue to extend survival and prolong or eliminate growth of tumors, such as metastatic tumors.

Furthermore, in some embodiments, recombinant technology can be used to develop a therapeutic fusion protein composed of a scorpion toxin, or a portion/derivative thereof, and a protein fragment that binds T cells (e.g., the ACDC1x fusion protein). The scorpion toxin derivative is considered safe in mammals. Its natural function is to disable invertebrate prey (insects), and has no known negative effects on mammals, with the exception that it has the ability to bind cells of neuroectodermal origin (e.g., tumor cells of a neuroectodermal origin). Because chlorotoxin can be produced using recombinant methods and not isolating it from the scorpion venom, there would be no chance of contamination of potentially harmful scorpion venom components. In one embodiment, the CD3-binding portion of the fusion protein proposed here is only specific for mouse T cells, with no known specificity to human T cells. As described herein, other embodiments provide for a fusion protein comprising an anti-CD3 binding portion that recognizes human and/or non-human animal T cells.

In some embodiments, administration (e.g., intravenous infusion) of an ACDC1x fusion protein would provide an effective antitumor effect in immune-competent subjects harboring invasive intracranial tumors by engaging the immune system against the tumor while avoiding healthy tissue. Chlorotoxin is coupled with a broad T cell binding antibody fragment (anti-CD3). CLx has a high specificity for cells of neuroectodermal origin, such as malignant cells and a remarkable ability to cross the BBB, allowing it to target the cancer cells present in the bulk tumor in addition to invasive cells that are intermingled with healthy tissue and are typically very difficult to treat. The ability of the anti-CD3 portion of ACDC1x to bind and activate some or all T cells circumvents the need for proper antigen presentation on the MHC complex, which is often absent in some forms of cancer, such as GBM. By coupling the Ctx and CD3-binding fragment together, the ACDC1x fusion protein is likely to activate resident T cells that are in close proximity with the tumor to initiate the formation of an immunological synapse, resulting in the direct transfer of cytotoxic granules from T cell to tumor.

In one embodiment, as disclosed herein, the ACDC1x fusion protein may be expressed in the tobacco relative *Nicotiana benthamiana*, a plant expression system. While mammalian and bacterial cell expression systems are most common, they are typically costly, require well-controlled conditions, and produce miniscule quantities at their best, typically on the order of micrograms from a single liter of culture, and may have issues producing proteins with disulfide bonds. Expressing ACDC1x in *N benthamiana* allows for the formation of disulfide bonds when targeted to the endoplasmic reticulum, the production of the fusion protein in microgram to milligram quantities from a single plant, and has the added benefit of less costly resources along with less stringent (greenhouse) growing conditions. Furthermore, producing ACDC1x in plants avoids potential contamination with human pathogens in the final product, something that is difficult to avoid in common mammalian and bacterial systems.

Expressing ACDC1x in plants can entail (1) designing and optimizing the DNA sequence of ACDC1x to promote high expression in plant cells and increase yield, (2), cloning the DNA sequence into a deconstructed viral-based vector and transfecting the resulting vector into a plant-specific class of bacteria called *Agrobacterium*, (3) infiltrating *N benthamiana* with the resulting *Agrobacterium* culture, (4) harvesting the protein from the leaf tissue after a pre-determined time, and (5) purifying the protein from any contaminating leaf or Agrobacterial proteins.

Agrobacteria serves as a natural delivery system to introduce the viral vector into the leaf tissue. Once in the tissue, the viral vectors may be engineered to spread easily from cell to cell, quickly replicating the gene of interest (GOI), ACDC1x. Both the ICON system and the Geminivirus system can initially be used to determine which produces the highest yield of ACDC1x. ICON is made of fragments of tobacco mosaic virus that allow for efficient replication of the GOI, and requires the transfection of three separate viral vectors into Agrobacteria. Thus, the GOI is expressed if all three components are present in the same plant cell. The ICON system has the benefit of being modular, allowing for the easy addition of signaling peptides, without the need to clone it into the vector containing the GOI. The Geminivirus system is a modified version of the Bean Yellow Dwarf Virus, with a circular genome that replicates via rolling circle transcription, thereby allowing for rapid expression of the protein. Once the protein has been harvested, it can be purified using a metal affinity column using a His-tag purification resin, which can bind strongly to a His-tagged protein. The ACDC1x sequence has been designed to display six histidine residues (His-tag) at the C-terminus for this purpose. Following column purification, the His tag can be cleaved off by a protease, the recognition sequence for which was also built into ACDC1x before the His-tag, and is part of the His-tag cleavage product.

In some embodiments, if desired, the protein can then be analyzed to verify structure and purity. Confirmation of Ctx and CD3 specificity can be demonstrated by a competitive binding assay with pure Ctx and full length anti-CD3 antibody, respectively, in GL261 cells and tissue slices obtained from mice bearing orthotopic tumors. The ability of ACDC1x to activate T cells and target tumor cells for destruction by T cells can also be tested in vitro, such as by co-culturing effector T cells with GBM cells in the presence of ACDC1x. T cell activation can be measured by cytokine release and tumor cell destruction can be measured using the lactose dehydrogenase release assay.

In one embodiment, the therapeutic effect of ACDC1x may be measured in vivo. The intracranial GL261-LucNeo model is a syngeneic, luciferase-expressing immune-competent mouse model that recapitulates many features of GBM, including the formation of a bulk tumor and subsequent invasion of cells into the normal brain tissue. An additional feature is the ability to monitor tumor growth quantitatively and non-invasively via bioluminescent imaging. This allows one of skill in the art to monitor tumor size over time to determine the ability of ACDC1x to reduce tumor size. The effect of ACDC1x on tumor burden and well-being can be measured by daily monitoring of weight, mobility, and presence of neurological symptoms.

In accordance with various embodiments herein, the invention describes a bi-specific antibody fusion protein, ACDC1x, comprising a Ctx domain and a CD3 binding domain (or anti-CD3 domain). The anti-CD3 domain is an immune stimulatory antibody fragment that can activate T cells, and this anti-CD3 domain can be coupled to Ctx (e.g., via a linker peptide), a cancer-targeting peptide (i.e., targeting cancers of a neuroectodermal origin). Ctx is capable of targeting both neuroectodermal primary tumor and cells that have invaded or metastasized beyond the primary tumor. The fusion protein can activate T cells in the vicinity of even small numbers of cancer cells, to direct their cytotoxic effects specifically to the target cells. In accordance with various embodiments herein, uses of the ACDC1x fusion protein may include, but not limited to, treatment of cancer by activation of T cells; or treatment of cancer by targeted therapy; or treatment of cancer by engaging with cancer cells that would have otherwise evaded detection and/or treatment.

Some embodiments provide significant benefits relative to standard of care treatments because immunotherapy has the strong potential to eradicate tumors, if immune cells can be properly activated and directed to the targeted cancer cells. The approach provided by some embodiments is capable of directing the immune response to small numbers of cancer cells (potentially individual cells), including cells of neuroectodermal origin. For the example of GBM, This approach could enable targeting cells that are located in areas in the brain where the BBB is at least partially intact. Specifically, this approach can overcome immune evasion by circumventing the need for MHC expression on the target cells. For other examples of neuroectodermal tumors (e.g., those in the periphery), this approach could enable much more specific therapy that avoids generating an undesired immune response against non-malignant cells or tissues.

The inventors describe an approach for targeted immunotherapy that links a T-cell activating antibody fragment to a tumor-targeting agent. The targeting agent provides targeting specificity for many different types of tumors (e.g., tumors of a neuroectodermal origin) and shows specificity for individual malignant cancer cells (i.e., those not associated with the primary tumor). As opposed to other antibody-based tumor targeting approaches, this fusion protein can target cells within a given tumor, not simply a fraction of the tumor that happens to express a protein of interest. Furthermore, evidence suggests that the targeting approach is not impeded by biological barriers such as the BBB, and so the fusion protein is capable of reaching cells that would otherwise escape either immune therapy or conventional chemotherapy. The T-cell activating agent has demonstrated use in other immunotherapy applications and is a potent and effective strategy for directing T cell cytotoxicity to cancer cells. The T-cell activating fragment has been used in humans in other configurations (i.e., without a Ctx domain), and this increases the expected safety. This approach does not require MHC expression on the malignant cells to engage T cells, which is an advantage in helping to overcome tumor cell immune evasion. In accordance with various embodiments herein, this fusion protein could be used clinically as a targeted immunotherapy.

In one embodiment, disclosed herein is a composition comprising a polypeptide with at least two domains, wherein the first domain is capable of binding CD3 on T cells and the second domain is capable of binding to a cancer cell. In one embodiment, the polypeptide is a single chain polypeptide.

In one embodiment, the cancer cell is of neuroectodermal origin. In one embodiment, the first domain comprises variable heavy (VH) and the variable light (VL) polypeptide chains of an anti-CD3 antibody. In one embodiment, the VH polypeptide comprises the sequence set forth in SEQ ID NO: 1 or SEQ ID NO: 2, or a polypeptide sequence having at least 50% sequence identity, more preferably at least 60% identity, more preferably at least 70% identity, more preferably at least 80% identity, more preferably at least 90% identity, more preferably at least 95% identity to SEQ ID NO: 1 or SEQ ID NO: 2. In one embodiment, the VL polypeptide comprises the sequence set forth in SEQ ID NO: 3 or SEQ ID NO: 4, or a polypeptide sequence having at least 50% sequence identity, more preferably at least 60% identity, more preferably at least 70% identity, more preferably at least 80% identity, more preferably at least 90% identity, more preferably at least 95% identity to SEQ ID NO: 3 or SEQ ID NO: 4. In one embodiment, the first domain further comprises a linker between VH and VL polypeptides. In one embodiment, the linker comprises the sequence set forth in SEQ ID NO: 5 or a polypeptide sequence having at least 50% sequence identity, more preferably at least 60% identity, more preferably at least 70% identity, more preferably at least 80% identity, more preferably at least 90% identity, more preferably at least 95% identity to SEQ ID NO: 5. In one embodiment, the first domain is derived from an antibody targeting human, non-human primate, or mouse CD3 receptor complex. In one embodiment, the second domain comprises a chlorotoxin peptide. In one embodiment, the second domain comprises a chlorotoxin-like peptide, such as CITx-a,b,c,d, BmKCL1, Lqh-8:6, Be ISA, Bell, AmrnP2 and GaTxl. In one embodiment, the second domain comprises a peptide having a sequence set forth in SEQ ID NO: 6 or SEQ ID NO: 7, or a polypeptide sequence having at least 50% sequence identity, more preferably at least 60% identity, more preferably at least 70% identity, more preferably at least 80% identity, more preferably at least 90% identity, more preferably at least 95% identity to SEQ ID NO: 6 or SEQ ID NO: 7. In one embodiment, the composition further comprises a polypeptide linker between the first and second domain. In one embodiment, the polypeptide linker has a sequence Gly-Gly-Gly-Gly-Ser, as set forth in SEQ ID NO 8. In one embodiment, the composition has a sequence as set forth in SEQ ID NO: 9, SEQ ID NO: 10, SEQ ID NO: 11, or SEQ ID NO: 12, or a polypeptide sequence having at least 50% sequence identity, more preferably at least 60% identity, more preferably at least 70% identity, more preferably at least 80% identity, more preferably at least 90% identity, more preferably at least 95% identity to SEQ ID NO: 9, SEQ ID NO: 10, SEQ ID NO: 11, or SEQ ID NO: 12. In one embodiment, the polypeptide described herein further comprises a protease cleavage sequence. In one embodiment, the nucleic acid sequence corresponding to the polypeptide described herein is set forth in SEQ ID NO: 13.

In one embodiment, disclosed herein is a method of treating cancer in a subject, comprising: providing a composition comprising a polypeptide with at least two domains, wherein the first domain is capable of binding CD3 on T cells and the second domain is capable of binding to a cancer cell; and treating the cancer by administering a therapeutically effective dosage of the composition to the subject. In one embodiment, the cancer cell is of neuroectodermal origin. In one embodiment, the cancer is glioblastoma (GBM). In one embodiment, the cancer cell comprises peripheral neuroectodermal tumors (PNET). In one embodiment, the cancer is medulloblastoma, neuroblastoma, ganglioneuroma, melanoma, adrenal pheochromocytoma, primitive PNET, small cell lung carcinoma, and/or Ewing's sarcoma. In one embodiment, the subject is human.

In one embodiment, disclosed herein is a method of expressing a protein' comprising: designing a DNA coding sequence corresponding to the protein; cloning the DNA coding sequence into a viral-based vector; transfecting the resulting vector into a plant specific class of bacteria; infiltrating a plant with the resulting bacteria culture; and harvesting the protein from the plant after a pre-determined time. In one embodiment, the protein comprises a polypeptide with at least two domains, wherein the first domain is capable of binding CD3 on T cells and the second domain is capable of binding to a target cell of neuroectodermal origin. In one embodiment, the protein is a recombinant single chain polypeptide comprising a domain capable of binding CD3, a linker, and cholorotoxin. In one embodiment, the protein further comprises six histidine residues (His-tag) at the C-terminus. In one embodiment, the method further comprises optimizing the DNA coding sequence to promote high expression and increased yield of the protein. In one embodiment, the viral based vector comprises a tobacco mosaic virus based vector, or a bean yellow dwarf virus based vector. In one embodiment, the plant specific class of bacteria is Agrobacteria. In one embodiment, the plant is *N benthamiana*. In one embodiment, the protein is harvested from a leaf tissue of the plant.

In one embodiment, disclosed herein is a transgenic plant system that expresses a fusion peptide comprising at least two domains, wherein the first domain is capable of binding CD3 and the second domain is capable of binding to a cancer cell. In one embodiment, a viral vector system may be used to turn on expression of the transgenes.

In one embodiment, disclosed herein is a method of purifying a recombinant protein expressed in a plant-based expression system comprising: blending plant tissues comprising the recombinant protein; centrifuging the blended tissues and discarding the supernatant; re-suspending the pellet in 1% Triton X-100, and discarding the supernatant; re-suspending and incubating the pellet comprising the recombinant protein in denaturing and/or reducing buffer; centrifuging and discarding the pellet; diluting the supernatant comprising the recombinant protein in refolding buffer; and concentrating the purified and refolded protein to the desired concentration. In one embodiment, the denaturing and/or reducing buffer comprises urea and DTT. In one embodiment, the urea is 8 M urea, and the DTT is 10 mM DTT. In one embodiment, the refolding buffer comprises Tris-HCl, NaCl, and oxidized L-glutathione.

As described herein, within the past five to ten years, immunotherapies have come to the forefront of cancer treatment, essentially revolutionizing the field of oncology. As is known to a skilled artisan, antibody therapy has continued to become more specific and effective. However, one major challenge with conventional immunotherapy is the high dose of antibody required to elicit a therapeutic effect in the brain.

As further disclosed herein, bispecific antibodies have been shown to harness the natural abilities of the patient's own immune system to target and treat tumor cells. However, no bispecific antibody targeting cancers of neuroectodermal origin has been developed and tested in an immunocompetent subject. The inventors have developed a novel fusion protein and/or polypeptide that will activate mature T cells against tumor cells. In one embodiment, the targeted immunotherapy will treat the tumor and/or decrease rate of tumor reoccurrence. In another embodiment, to achieve this, the inventors linked chlorotoxin, a peptide that binds cancer cells of neuroectodermal origin with specificity, to the T-cell activating antibody fragment of anti-CD3. Some embodiments provide a composition comprising an ACDC1x compound. In one embodiment, the ACDC1x compound comprises a polypeptide with two domains—an anti-CD3 binding domain and a chlorotoxin peptide domain. In another embodiment, the present disclosure provides a method of treating cancer, comprising providing a composition comprising an ACDC1x compound, and treating the cancer by administering a therapeutically effective dosage of the composition to a subject. In another embodiment, the cancer is of neuroectodermal origin, such as GBM.

In various embodiments, the present invention provides pharmaceutical compositions including a pharmaceutically acceptable excipient along with a therapeutically effective amount of an ACDC1x fusion protein, or a pharmaceutical equivalent thereof "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intracranial, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. In one embodiment, "parenteral" contemplates injection into the parenchyma of the brain.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. In one embodiment, the encapsulation comprises encapsulating the composition in a nano or micro particle for polymeric drug delivery. The invention or the carrier of the invention may undergo additional chemical modification to further alter or enhance its distribution and potency. In one embodiment, such modification could include attachment of a poly-ethylene glycol or other co-sti11ulatoly url.,;u-largeting molecules. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax. The carrier may also include a polymer.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Typical dosages of a composition that may be used, for example of a targeted immunotherapy can be m the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models.

The present invention is also directed to a kit to treat cancer and prepare various targeted immunotherapeutic compounds. The kit is an assemblage of materials or components, including at least one of the inventive compositions. Thus, in some embodiments the kit contains a composition including one or more ACDC1x fusion proteins, as described above.

The exact nature of the components configured in the inventive kit depends on its intended purpose. For example, some embodiments are configured for the purpose of treating cancer, including GBM. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing ACDC1x.

The packaging material generally has an external label which indicates the contents and/or purpose of the kit and/or its components.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein.

Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, 1t 1s merely for purposes of illustration and is not intended to limit the invention. One skilled in the art may develop equivalent means or reactants without the exercise of inventive capacity and without departing from the scope of the invention.

Example 1

Purification

Following large scale expression of ACDC1x in plants, a His-tag purification resin may be used to purify ACDC1x from other components (proteins and other molecules) that might have carried through after processing the plant material so that it can be used for in vitro and in vivo experiments. ACDC1x may be designed to be expressed with six histidine residues at the C-terminus of the protein, a modification known as His-tagging. When passed through a column containing a cobalt or nickel based His-tag purification resin, the His tag tightly binds the cobalt or nickel component of the resin, while other proteins and molecules from the protein preparation pass through. Using a solvent known as imidazole, the bound ACDC1x can be washed off the resin and collected into a sample vessel for further downstream purification and analysis.

As will be apparent to one of skill in the art, the plasmid vector for expression of the recombinant protein disclosed herein, when translated, may not contain a histidine tag at the C-terminus, or may contain a different tag useful for protein purification. In those cases, methods of purification may involve another resin besides the His-tag purification resin. Such modifications in protein purification protocols are commonly known to a skilled artisan in the art.

Example 2

Functionality

After purification of ACDC1x, the fusion protein can be evaluated for target specificity using in vitro assays. The competitive binding assay is a practical method to measure functionality for Ctx and the CD3 binding domain. To assay for CD3 specificity, one could incubate CD3-positive T cells in culture with varying concentrations of ACDC1x prior to incubation with anti-CD3 antibody. In samples where the ACDC1x concentration is high, one could expect the fusion protein to outcompete anti-CD3 antibody for the epitope they both share, thereby blocking the ability for anti-CD3 antibody to bind to the T cells. One could detect the relative amount of anti-CD3 antibody bound to the cells across the different conditions by incubating with a fluorescently-labeled secondary antibody. In controlled conditions, the fluorescence detected will be proportional to the relative amount of anti-CD3 antibody that is bound to the T cells. In conditions of increasing concentrations of ACDC1x, there will be observed little to no fluorescence, compared to T cells that were not pre-incubated with ACDC1x. This would indicate, for example, that ACDC1x is specifically binding to CD3 on the T cells.

The anti-CD3 antibody can also be used as a positive control for the cytokine release assay. The cytokine release assay can be used to evaluate the capacity for ACDC1x to activate T cells in vitro. The anti-CD3 2Cll clone is commonly used in functional assays to activate T cells by crossslinking CD3 on the T cell surface, thereby stimulating the release of cytokines, such as IL-2. One can therefore determine the extent to which T cells are activated following incubation with ACDC1x and cancer cells by measuring IL-2 secreted into cell culture media, and comparing it to T cells that have been incubated with anti-CD3 antibody. One can expect IL-2 levels to be relatively high in cultures that have been incubated with ACDC1x and cancer cells or anti-CD3 antibody, and IL-2 levels to be low in cultures that have been incubated with Ctx alone or buffer.

Example 3

Design of the Construct

The coding sequences for the fusion protein (SEQ ID Nos: 9, 10, 11 and 12) were optimized for plant expression by choosing frequently used codons within the plant system. This sequence was synthesized and inserted into a Geminiviral vector based on the bean yellow dwarf virus. These elements were found to increase the expression using multiple methods, including increasing DNA amplification, suppression of plant-mediated gene silencing, and improving nuclear matrix attachment. While this approach was used to design a construct described herein, a skilled artisan in the art would know that may be alternate approaches that would also be effective at achieving protein expression. A barely alpha amylase (BAA) signaling sequence is inserted immediately upstream of the ACDC1x coding sequence to target the translated protein to the endoplasmic reticulum. This is to allow for the formation of disulfide bonds within the chlorotoxin peptide sequence.

Example 4

Production and Purification

Infiltration:

*Agrobacterium tumefaciens* (strain EHA105) were transformed with the pBYR2ek2Mc-3Ctx vector. The transformed bacteria were infiltrated into the leaves of 5-7 week old *Nicotiana benthamiana* at an optical density (OD) of 0.2.

Harvesting, Extraction, Purification, and Refolding:

Infiltrated leaf tissue was harvested four days post infiltration (DPI) and weighed. Several steps are performed to reduce the overall non-ACDC1x protein content in the sample to improve purity in the final steps. The tissue was blended in ice cold PBS (2.5% w/v), strained, and centrifuged to remove the soluble protein fraction in the resulting supernatant. The pellet was re-suspended in 1% Triton X-100 (25% w/v) and centrifuged to remove membrane-bound proteins in the supernatant. The pellet ("Triton-insoluble fraction") containing ACDC!x was re-suspended in denaturing/reducing buffer (8M urea, 10 mM DTT, 50 mM Tris-HCl pH 8, 0.5M NaCl) and incubated for two hours at 4° C., with quick vortex and water bath sonication every 10 minutes. This process dissociates, unfolds, and reduces disulfide bonds within proteins. The solution containing ACDC!x was briefly centrifuged to remove any large particulates and the supernatant was incubated with His-tag purification resin overnight. The next day, the resin was washed of proteins and molecules not bound to the resin, and ACDC1x was refolded on column with decreasing concentration sof urea in refolding buffer (50 mM Tris-HCl pH 8, 0.5M NaCl, 0.5 mM oxidized L-glutathione). ACDC1x was eluted from the column with 850 mM imidazole in 50 mM Tris-HCl pH 8, 0.5M NaCl.

As illustrated in FIG. 1, ACDC!x is found in the triton-insoluble fraction, after solubilizaition in denaturing and reducing buffer (8M urea and 10 mM DTT). In one embodiment, ACDC!x (32 kDa) was not present in the soluble fraction (XT) or the triton-soluble fraction (TS). In one embodiment, the Triton insoluble fraction was solubilized in buffer containing 8M urea and 10 mM DTT.

As illustrated in FIG. 2, ACDC!x is not detected under non-reducing conditions, suggesting the His-tag may be folded inside of the fusion protein. Solubilized ACDC1x and the resulting eluates were analyzed via Western blot. Samples were prepared in denaturing/reducing conditions (SDS, DTT, boiled 5 minutes) (+) or semi-non-denaturing, non-reducing conditions (SDS, no DTT, not boiled) (−). ACDC1x is not detected with an anti-His antibody under non-reducing conditions.

As illustrated in FIG. 3, optimization of Tris-HCl pH illustrates that ACDC!x is eluted in the greatest yield using pH 7.5 and 8. ACDC1x was solubilized in 8M urea and purified using a His-tag purification resin. The pH of 50 mM Tris-HCl was varied for each purification to determine the optimal pH, and Western blots were prepared from the eluates. The different lanes correspond to pH 8, 7, 7.5, 8.5, and 9, respectively. The greatest eluate yield was observed using pH 8 and 7.5.

As illustrated in FIG. 4, addition of OTT does not reduce the solubilization efficiency of ACDC1x, and thus is a good candidate for use as a reducing agent prior to refolding. Different combinations of 8M urea and 10 mM DTT were used to determine extraction efficiency in each. Extraction in 8M urea with DTT is at least equally efficacious as 8M urea alone. Extraction in DTT alone is much less efficient. SN=solubilized fraction. P=pellet (insoluble fraction).

As illustrated in FIG. 5, ACDC1x can be detected in the eluates following purification and refolding on-column.

As illustrated in FIG. 6, an example of the purity of ACDC1x that can be obtained after a His-tag purification. Protein content was resolved under reducing (left) and non-reducing conditions (right).

Example 5

Illustrative Roles and Functions of the Recombinant Fusion Protein, ACDC1x

In one embodiment, the disclosure herein illustrates that Anti-CD3/Ctx (ACDC1x) can serve as an enhancer of T cell recognition of GBM cells and other malignant cells of neuroectodermal origin. This enhancement would allow the T cells to bypass stringent requirements for the initiation of cytotoxic processes against cells if both cancer cells and T cells are bound by ACDC1x. This allows any T cells in the tumor periphery to directly kill tumor cells, rather than first requiring T cell recognition of a specific antigen presented by the tumor. Further responses by the T cells may then be independent of the ACDC1x fusion protein due to subsequent recognition of released tumor antigens.

ACDC1x is expressed as a single polypeptide chain and is composed of the variable heavy and light regions (VH and VL) from an anti-CD3 antibody (hamster anti-mouse, clone 2C1 1), fused to the peptide chlorotoxin. VH and VL are connected using a (Gly4Ser)3 peptide linker commonly used as an inert spacer for protein fusions. Three Gly4Ser elements are used to promote the flexibility and binding capabilities of the anti-CD3 portion to CD3, which is expressed on the surface of all mature T cells. The anti-CD3 portion is linked to chlorotoxin, which was shown to bind to all GBM samples tested (n=3 1) and over 96% of all other primary brain tumor samples tested (See S. A. Lyons et al, Chlorotoxin, a scorpion-derived peptide, specifically binds to gliomas and tumors of neuroectodermal origin, Glia. 39 (2002) 162-173). Chlorotoxin was also shown to be specific for other tumors of neuroectodermal origin, including melanoma and small cell lung carcinoma. Furthermore, no binding of chlorotoxin was found on any healthy tissues, including healthy brain.

ACDC1x is designed to serve as a bridge that can provide a direct connection between a T cell and a targeted tumor cell. This will engage the T cell to kill the tumor cell quickly using cytotoxic granules (CD8+ T cells) or slowly by initiating other apoptotic signaling pathways (CD4+ T cells). T cell-mediated killing is activated by the engagement of CD3, which permits a polyclonal T cell response. T cells typically require two distinct interactions with a target cell prior to killing, which limits their toxicity in vivo. A variable protein complex on the T cell called a T cell receptor (TCR) must recognize an MHC complex on the target cell as well as a peptide presented on the MHC protein. Each TCR is specific for a single antigen, and only one form of TCR is expressed on a single T cell. This limits each T cell to recognize only a single antigen, which must be expressed on the target cell to initiate T cell killing (a monoclonal T cell response). When these requirements are met, i.e., when the TCR recognizes a self MHC protein presenting its cognate peptide, the T cell is then activated to kill the target cell.

The activation described above occurs through signaling downstream of CD3 activation. Thus, ACDC1x is able to help T cells overcome the TCR-peptide-MHC requirement by directly engaging and activating CD3 while simultaneously binding a target tumor cell. Furthermore, the activation of CD3 can only occur when the T cell is directly bound to a target cell, as the activation of CD3 is dependent on applied force. This provides the basis for a single Gly4Ser linker (rather than a longer linker) between anti-CD3 and chlorotoxin, which will enable very close contact between the T cell and target cell for efficient T cell killing.

Example 6

Cancer Cells

FIGS. 7 and 8 illustrate the effect of the recombinant fusion protein ACDC1x on cancer cells.

As illustrated in FIG. 7, calcium flux (as indicated by an increase in Fluo-4 AM fluorescence intensity using FITC excitation/emission filter) was measured immediately after mixing GL261-LucNeo mouse glioma cells with freshly isolated mouse splenocytes with (1) nothing adding, (2) ACDC1x protein buffer (no ACDC1x), or (3) ACDC1x added. Calcium flux is an indicator of initial T cell activation. Three equivalent samples were measured consecutively: Splenocytes+GL261 cells (nothing added); Splenocytes+GL261+protein butler; and Splenocytes+GL261+ACDC1x.

As illustrated in FIG. 8, CD4+ and CD8+ T cell activation was measured by CD69 expression 11 hours post-treatment. The treatment comprised: Media (negative control), 1 ug/mL ACDC1x, or anti-CD3 antibody (positive control). Treatments were incubated with freshly isolated mouse splenocytes (B6 background) and confluent GL261-LucNeo mouse GBM cells.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of treating cancer in a subject, comprising:
providing a composition comprising a polypeptide with at least two domains, wherein the first domain is capable of binding CD3 and the second domain comprises a chlorotoxin peptide and/or a chlorotoxin-like peptide and is capable of binding to a cancer cell;
wherein the composition includes a sequence comprising SEQ ID NO: 9. SEQ ID NO: 10, SEQ ID NO: 11, or SEQ ID NO: 12; and
treating the cancer by administering a therapeutically effective dosage of the composition to the subject.

2. The method of claim 1, wherein the cancer cell is of neuroectodermal origin.

3. The method of claim 1, wherein the cancer is glioblastoma multiforme (GBM).

4. The method of claim 1, wherein the cancer cell comprises peripheral neuroectodermal tumors (PNET).

5. The method of claim 1, wherein the cancer is medulloblastoma, neuroblastoma, ganglioneuroma, melanoma, adrenal pheochromocytoma, primitive PNET, small cell lung carcinoma, and/or Ewing's sarcoma.

6. The method of claim 1, wherein the subject is a mammal.

7. The method of claim 1, wherein the subject is a human.

8. The method of claim 1, wherein the composition is administered to the subject intravenously.

9. The method of claim 1, wherein the composition is administered to the subject intracranially.

10. The method of claim 1, wherein the composition is administered directly to the cancer cells of the subject.

11. The method of claim 1, wherein the first domain comprises variable heavy (VH) and the variable light (VL) polypeptide chains of an anti-CD3 antibody.

12. The method of claim 11, wherein the VH polypeptide comprises a sequence having SEQ ID NO: 1 or SEQ ID NO: 2.

13. The method of claim 11, wherein the VL polypeptide comprises a sequence having SEQ ID NO: 3 or SEQ ID NO: 4.

14. The method of claim 1, wherein the second domain comprises a polypeptide with a sequence having SEQ ID NO: 6 or SEQ ID NO: 7.

15. The method of claim 1, wherein the composition further comprises a polypeptide linker between the first and second domain.

16. The method of claim 15, wherein the polypeptide linker has a sequence Gly-Gly-Gly-Gly-Ser, as set forth in SEQ ID NO 8.

* * * * *